Figure 1:
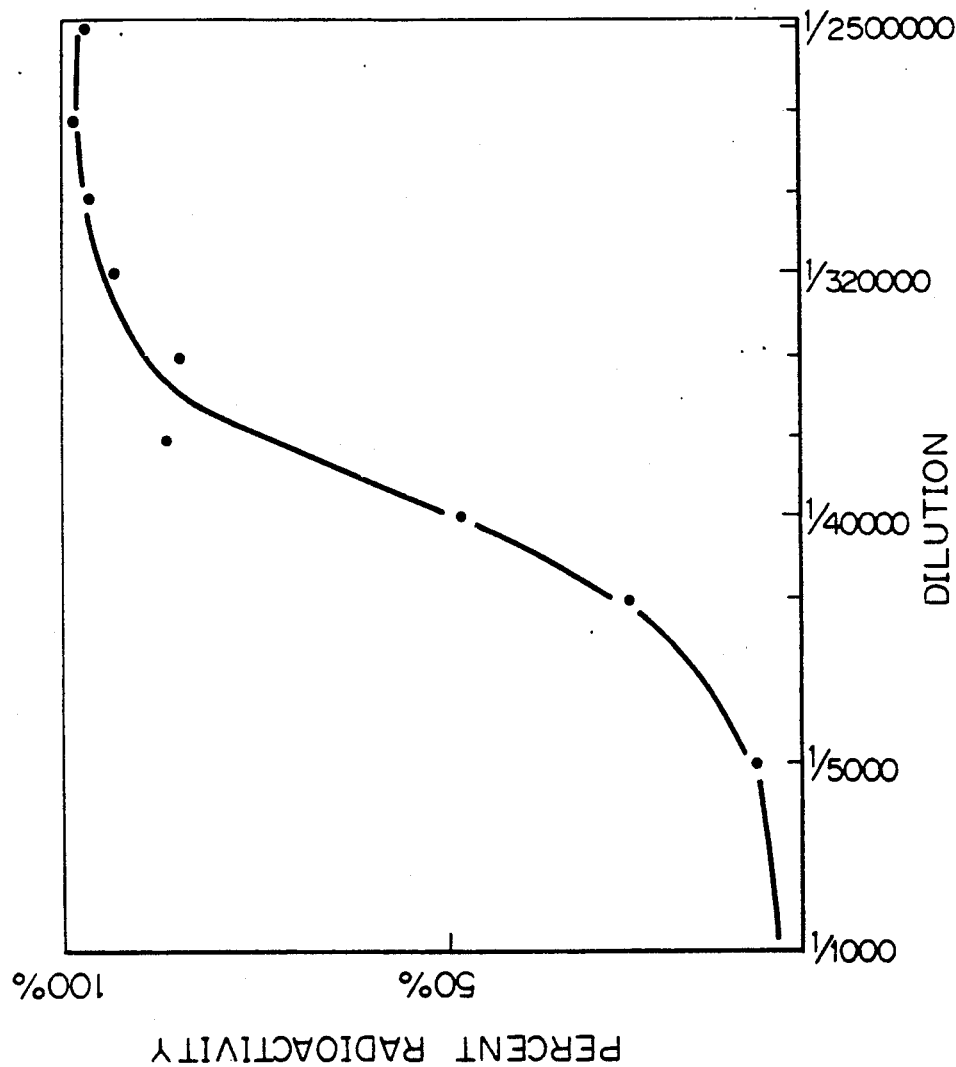

United States Patent [19]

Shiosaka et al.

[11] Patent Number: 5,112,606

[45] Date of Patent: May 12, 1992

[54] METHOD OF PRODUCING ANTIBODIES USING COLLOIDAL METAL AS CARRIER

[76] Inventors: Sadao Shiosaka, 402-671 William Ave., Winnipeg, Manitoba, R3E 0Z2, Canada; Johji Kohno, 5-5-4, Fujisawadi, Tondabayashi-shi, Osaka, Japan; Hiroshi Kiyama, 4-27-506, Shimoyoshiwar, Nishinomiya-shi, Hyogo-ken, Japan; Masaya Tohyama, 2-9-3, Shinsenrikitamachi, Toyonaka-shi, Osaka, Japan; Yahe Shiotani, 2-3, Uoyamachi, Kishiwada-shi, Osaka, Japan

[21] Appl. No.: 414,608

[22] Filed: Sep. 29, 1989

Related U.S. Application Data

[63] Continuation of Ser. No. 1,860, Jan. 9, 1987, abandoned.

[30] Foreign Application Priority Data

Jan. 10, 1986 [JP] Japan .................................. 61-3825

[51] Int. Cl.$^5$ .................... A61K 39/395; C07K 15/28
[52] U.S. Cl. ............................... 530/389.2; 530/387.1; 530/388.9; 530/389.9; 435/960; 436/547; 436/548
[58] Field of Search ............... 424/85.8, 86, 87, 88, 424/89, 90, 91, 92, 93; 514/2, 8, 10, 21; 530/387, 388, 391, 806, 808

[56] References Cited

U.S. PATENT DOCUMENTS

| | | | |
|---|---|---|---|
| 3,919,413 | 11/1975 | Mebus | 424/89 |
| 4,016,252 | 4/1977 | Relyveld | 424/89 |
| 4,196,185 | 4/1980 | Focella et al. | 530/387 |
| 4,197,237 | 4/1980 | Leute et al. | 530/387 |
| 4,197,286 | 4/1980 | Rao | 530/387 |
| 4,213,964 | 7/1980 | Buckler | 530/387 |
| 4,215,036 | 7/1980 | Malley | 424/88 |
| 4,218,436 | 8/1980 | Fitzpatrick | 530/387 |
| 4,329,281 | 5/1982 | Christenson et al. | 530/387 |
| 4,332,787 | 6/1982 | Homcy et al. | 530/387 |
| 4,346,074 | 8/1982 | Gilmour et al. | 424/92 |
| 4,578,270 | 3/1986 | Csizer et al. | 424/92 |
| 4,608,252 | 8/1986 | Khana et al. | 424/85.8 |
| 4,639,336 | 1/1987 | Jouguey et al. | 424/85.8 |

FOREIGN PATENT DOCUMENTS

| | | | |
|---|---|---|---|
| 0156242 | 10/1985 | European Pat. Off. | 424/89 |
| 2533827 | 4/1984 | France | 424/89 |
| 981242 | 1/1956 | United Kingdom . | |

OTHER PUBLICATIONS

Erlanger, Methods Enzymol., vol. 70, pp. 85-104, (1988).
Chem. 46 88(13): 87448r, Romano et al., 1978.
Chem. Ab 101: 51404w, Petrie et al., 1984.
Chem. Ab 104: 62641; Van den Pol, 1986 (1985 pub date).
Chem. Abs 105: 188923s, 1986, Shiosaka et al.
Microbiology Abstracts Section B (Dec., 1969), p. 145, No. B1934.
Textbook of Immunology: Benacerraf, et al.; pp. 1-17.
Neurohistochemistry: Modern Methods & Applications; Steinbusch et al., pp. 74-81.
Anatomy of Putative Glutamatergic Neurons; Storm-Mathisen et al., pp. 39, 44-47.

*Primary Examiner*—John Doll
*Assistant Examiner*—Paula Hutzell
*Attorney, Agent, or Firm*—Cushman, Darby & Cushman

[57] ABSTRACT

The present invention relates to methods of producing an antibody highly specific to a low-molecular weight substance such as amino acids, peptides, amines, steroids, etc. The invention also relates to a process for producing the same by forming a complex of the substance with colloidal metal particles and sensitizing a mammal with the complex. The antibody can be in the form of an antiserum containing the antibody. Since the antibody has a high specificity to the intended low-molecular weight substance, it is useful as a reagent for various immunohistochemical methods and immunoassays.

5 Claims, 1 Drawing Sheet

METHOD OF PRODUCING ANTIBODIES USING COLLOIDAL METAL AS CARRIER

This is a continuation of application Ser. No. 07/001,860, filed Jan. 9, 1987, which was abandoned upon the filing hereof.

This invention relates to an antibody having high specificity which is useful in the field of immunohistochemistry and immunoassay. This invention also relates to an antiserum containing the antibody and a process for producing the antibody.

Immunohistochemical techniques and immunoassays have been broadly used in research and the clinical field for accurately, sensitively and specifically detecting the distribution of or level of a physiologically active substance such as a hormone. What is most important if such methods are to be conducted appropriately is to obtain an antiserum having a high specificity and a high titer. It has been relatively easy to obtain a highly specific antiserum with respect to a protein or glucoprotein having a high molecular weight. However, it has been very difficult to provide an antiserum having a high specificity against substances of lower molecular weights such as amino acids, low-molecular weight peptides and the like, because such substances have lower antigenicity or lower immune responsivities. That is, these substances cannot cause an immune response in vivo before they are bound to an appropriate carrier, or can induce only weak immune response if any. In the prior art, attempts have been made to increase the immune responsivity of low-molecular weight substances as antigens by cross-linking them with a proteinaceous carrier such as bovine serum albumin, hemocyanin, thyroglobulin, etc. with a cross-linking agent such as 1-ethyl-3-(aminopropyl)carbodiimide (CDI), glutalaldehyde, formaldehyde, or by adsorbing the substances on a support such as polybinylpyrrolidone. However, these trials have not brought about any improvement with respect to decreases in the specificity of the antibody produced, because antibodies against the protein used as a carrier or cross-linking agent are produced concurrently with the production of the intended antibody during the immune reaction, and these undesirable antibodies reduce the specificity of the intended antibody.

Especially, in the case of a low-molecular weight substance such as an amino acid, amine, acetylcholine, etc. being used as an antigen, no antibody against such substance alone has been produced, except for antibodies against the complexes of the substance with the cross-linking agent or the proteinaceous carrier. In order to identify such lowmolecular weight substance in immunohistochemistry, the antibody against the complex has been used in spite of its low specificity by fixing the antibody on the same material as that of the cross-linking agent or carrier used in the production of the antibody.

The inventors of this invention first found a novel method for producing a highly specific antibody against a substance having a low molecular weight such as amino acids, amines, acetylcholine, peptides and the like without using a cross-linking agent. According to the method of this invention, the substance having a low molecular weight is bound on the surface of colloidal metal particles by ionbonds based on the facial charge of the particles. Since no cross-linking agent is used and the colloidal metal has low antigenicity, the production of antibodies other than ones which are active against the target substance can be kept to a low level whereby the antibody against the target substance may be specifically produced.

FIG. 1 shows the test results with respect to the ability of an antigen (glutamic acid) to bind with its antibody produced according to the method of this invention. In the graph, the transversal axis represents a series of dilution of the antiserum, and the vertical axis shows the ratio (%) of the radioactivity of free form of glutamic acid remaining in a supernatant to the total activity. The higher the concentration of the antiserum is (the left hand side in the graph), the higher is the level of radioactivity of the antibody-binding glutamic acid (the radioactivity of precipitate obtained by centrifugation at 12,000 rpm.), and concurrently the lower is the level of the radioactivity of the free form of glutamic acid.

According to the method of this invention, a cell having a gene capable of producing such an antibody as described above (the cell being referred to as a clone hereunder) can be produced in vivo in a mammal. In addition, it is possible to take the clone out of the mammalian body and to utilize it to produce the target antibody in vitro. Namely, the clone is fused to an appropriate tumor cell to form a hybridoma which can be kept alive forever, and the antibody can be produced from this hybridoma.

Accordingly, this invention provides a method of producing an antibody by using the clone described above.

This invention also provides immunohistochemical methods or immunoassays which use the antibody obtained in the above manner or an antiserum containing that antibody. These methods or assays can be conducted by utilizing the binding between the antibody and the low-molecular weight substance which was used as an antigen, because the antibody has a high specificity against that substance. The substance acts as an antigen and is bound to the antibody by the antigen-antibody reaction. Examples of the immunohistochemical methods and immunoassays which can be conducted by using the antibody produced according to this invention are immunohistochemical techniques such as a fluorescent antibody technique, an enzyme-labelled antibody technique, a peroxidase anti-peroxidase staining technique, an avidinbiotin complex technique (ABC technique), or an avidinbiotin technique (AB technique); and immunoassays such as radioimmunoassays and non-isotope immunoassays in which substances other than isotopes such as enzyme-ELSA, a metal ion, a fluorescent substance, a chemiluminescent substance or the like is used as a label.

The present invention can be applied not only to a low-molecular weight substance as an antigen but also to a high-molecular weight substance such as proteins, glucoproteins and the like. Such a high-molecular weight substance is bound to colloidal metal particles to make the production of an antibody against that substance easy.

Examples of low-molecular weight substances to which this invention is preferably applied are amino acids such as glutamic acid and aspartic acid; amines such as serotonin, noradrenaline, histamine, and the like; steroids such as testosterone, acetylcholine and their derivatives; metabolic intermediates; and peptides such as peptide hormones and peptides composed of their active centers.

Colloidal metals which are useful in this invention are prepared by conventional methods, for example, for preparation of colloidal gold, Frens, "Nature" 241, 20–22 (1973); Stathis and Fabrikanos, "Chem. Ind." (London) 27, 860–861 (1958); and Baigent and Muller, "Experientia" 36, 472 (1980); for colloidal iron, Kreke, "J. Prat." 3, 286 (1974); and Grimaux, "Ber. Dtsch. Chem. Ges." 17, 104 (1884); and for colloidal aluminum hydroxide, Muller, "Z. Anorg. Chem." 57, 311 (1908).

When a radical having a positive charge such as $-NH_3^+$ is utilized to bind the substance having such radicals to the surface of the colloidal particles, colloidal gold is preferably used because its surface has negative charges. On the other hand, for binding a radical having negative charges such as $-COO^-$, colloidal iron which has positive charges on its surface may be conveniently used.

It is considered that the substance used as an antigen would be bond to the colloidal particles by a force such as Van der Waals force as well as ion bonds. However, the mechanism behind the binding which occurs has not yet been completely understood.

This invention is illustrated in detail by the following Examples.

EXAMPLE 1

Colloidal gold was prepared by the method of Frens. That is, 4 ml of a 1% sodium citrate solution was added to 100 ml of a 0.01% tetrachloroauric acid aqueous solution, and the mixture was boiled to form colloidal gold particles having a diameter of from 13 to 15 nm with the aid of the reducing power of the citrate.

After cooling, the colloidal gold solution was mixed with a glutamic acid aqueous solution having a concentration of 5 mg/ml to form stable complexes. Before mixing, the two solutions were adjusted to bring their pH to about 9.0 and about 9.5, respectively, by using a 0.2 M - $K_2CO_3$ aqueous solution. The mixing ratio corresponded to a proportion of 1 to 1.5 ml of the glutamic acid solution per 1 ml of the colloid solution. The complexes were used for production of an antibody of glutamic acid. Under these conditions, the colloidal gold, which will aggregate if NaCl is added to the solution at a final concentration of 0.5 to 0.9%, was stabilized by forming complexes with glutamic acid. It was found that these complexes did not aggregate even in the presence of NaCl at the above-mentioned concentration. The solution of the stabilized complexes (1 ml) was mixed with 1 ml of the Freund's complete adjuvant to form an emulsion. The emulsion was subcutaneously injected in several tens of locations on a rabbit is body in a dose of 0.1 to 0.2 ml per location. The treatment was repeated 4 times every 2–3 weeks. Ten days after the 4th injection, blood was sampled from the rabbit and serum was separated from it. The properties of the serum were analyzed, and it was found, as shown in FIG. 1, that the sample was an antiserum having such a very high titer that the antiserum diluted by 50,000 –80,000 times exhibited an ability to bind 50% of the total amount of $^{14}C$-glutamic acid which was added.

Furthermore, the sample was also subjected to tests to determine the cross-reactivity against substances other than glutamic acid. It was confirmed that the sample exhibited a 100% cross-reactivity against α-glutamyl-glutamic acid, but did not show substantial cross-reactivity against aspartic acid which is analogous in structure to glutamic acid.

On the other hand, when the central nervous system was stained with the antiserum, it showed very high staining ability. These results proved that the antiserum is very useful in the field of immunohistochemistry.

These test results as explained above were confirmed by repeating the tests, conducting them with several rabbits.

EXAMPLE 2

By a procedure similar to that of Example 1, a specific antiserum was produced by using, as an antigen, each of aspartic acid, glycine, taurine and acetylcholine. The test results of each of these antiserums with respect to their properties proved to be almost the same as those of Example 1.

Incidentally, the pH of a solution of colloidal gold and the antigen was 7.0, and the ratio by volume of colloidal gold to the antigen was 1:1 for aspartic acid, a pH of 5 and a ratio of 1:2 for glycine, a pH of 7 and 1:10 for taurine, and a pH of 7 and 1:2 for acetylcholine.

We claim:

1. A method of producing an antibody specific for a substance selected from the group consisting of an amino acid, taurine, acetylcholine, serotonin, noradrenaline, histamine and a steroid, which comprises
   (i) adsorbing the substance onto colloidal gold in the absence of any additional agents or carriers,
   (ii) administering the complex to a mammal to induce an immune response against the substance, and
   (iii) isolating either the antibody producing cells, or the antiserum from the immunized mammal.

2. A method according to claim 1 wherein the amino acid is selected from the group consisting of glutamic acid, glycine and aspartic acid.

3. A method according to claim 1 wherein the substance is selected from the group consisting of taurine and acetylcholine.

4. A method according to claim 1 wherein the substance is selected from the group consisting of serotonin, noradrenaline, histamine.

5. A method according to claim 1 wherein the steroid is testosterone.

* * * * *